United States Patent [19]

Craig et al.

[11] Patent Number: 4,608,082

[45] Date of Patent: Aug. 26, 1986

[54] HERBICIDAL CYCLOALKENYL ACETAMIDES

[75] Inventors: Todd A. Craig, Raleigh; John J. Jachetta, Pittsboro, both of N.C.

[73] Assignee: Union Carbide Corporation, Danbury, Conn.

[21] Appl. No.: 702,652

[22] Filed: Feb. 19, 1985

[51] Int. Cl.[4] .................... A01N 37/18; C07C 103/37
[52] U.S. Cl. ................................ 71/118; 71/98; 71/103; 71/105; 260/503; 558/49; 558/430; 558/431; 564/210; 564/217
[58] Field of Search ............. 71/105, 118, 98, 103; 564/210, 217; 260/464, 503; 558/49, 430, 431

[56] References Cited

U.S. PATENT DOCUMENTS

| | | | |
|---|---|---|---|
| 3,586,496 | 10/1969 | Chupp | 71/118 |
| 4,319,918 | 3/1982 | Baltruschat et al. | 71/118 |
| 4,351,667 | 9/1982 | Chupp | 71/118 |

FOREIGN PATENT DOCUMENTS 3245020  6/1984  Fed. Rep. of Germany .

*Primary Examiner*—Dolph H. Torrence
*Attorney, Agent, or Firm*—Daniel Reitenbach; Clement J. Vicari

[57] ABSTRACT

This invention relates to novel herbicidal cycloalkenyl acetamides. These acetamides are useful in the inhibition of undesired vegetation and exhibit excellent selectivity in crops of cultivated plants, particularly in crops of flooded rice.

27 Claims, No Drawings

HERBICIDAL CYCLOALKENYL ACETAMIDES

FIELD OF THE INVENTION

This invention relates to novel herbicidal cycloalkenyl acetamides that exhibit broad-spectrum activity, high potency and improved selectivity with respect to dry-land crops and crops of flooded rice.

BACKGROUND OF THE INVENTION

There are two common systems of rice cultivation in use today: the dry system wherein the crop is grown on dry ground and the wet system wherein the crop is planted, or transplanted, and grown in a flooded field. The wet system is the most prevalent due to the severe weather patterns in the major rice growing areas of the world. For example, over 90% of the world rice production is grown in Asia which has a pronounced monsoon season.

Although flooding itself can help reduce weed populations, some fields, such as those in large areas of south and southeast Asia, cannot be flooded continuously and therefore effective weed control practices are essential for efficient farming. The usual procedures for herbicide application involve removing the water from the field one or two days before the application of the herbicide; applying the herbicide; and then flooding the field again approximately two days after the herbicide has been applied.

Flooding can significantly affect the distribution, stability and residual activity of an herbicide in the soil. The anaerobic conditions common in flooded soils can adversely affect the chemical stability, and consequently the utility, of the herbicide. Furthermore, an herbicide will not necessarily remain in the soil layers of a flooded field. Movement of the herbicide from the soil into the water and the potential loss of the herbicide by codistillation can severely reduce the herbicide's effectiveness. The discovery and development of herbicides that are useful in this unique situation are therefore important concerns.

Certain substituted cycloalkenyl acetamides are useful as active ingredients in herbicidal compositions. Such herbicidal acetamides are disclosed, for example, in U.S. Pat. No. 3,586,496; 4,319,918 and 4,351,667 and in German Patent Application No. DE 3245020A1. Prior to the present invention, however, none of these known herbicidal cycloalkenyl acetamides exhibited an acceptable level of selectivity with respect to crops of flooded rice.

Accordingly, it is an object of the present invention to provide novel herbicidal cycloalkenyl acetamides which combine broad spectrum activity, high potency and improved selectivity for crops of cultivated plants. Moreover, it is an object of this invention to provide a novel class of herbicides which exhibit a remarkable degree of selectivity with respect to crops of flooded rice as well as dry-land crops.

DESCRIPTION OF THE INVENTION

This invention is directed to cycloalkenyl acetamides which exhibit broad-spectrum herbicidal activity, high potency and show an excellent degree of selectivity for crops of cultivated plants, such as soybeans, corn, cotton and most particularly, flooded rice.

The herbicidal compounds of this invention can be represened by the following generic formula:

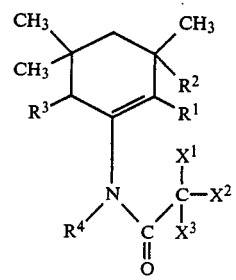

wherein
  $R^1$ and $R^3$ are individually hydrogen; cyano; or alkyl, alkenyl, alkoxyalkyl, cyanoalkyl or haloalkyl of from 1 to 10 carbon atoms, linear, branched or cyclic;
  $R^2$ is hydrogen; alkyl, alkoxyalkyl, alkenyl, alkynyl, haloalkyl, cyanoalkyl or haloalkenyl of from 1 to 10 carbon atoms, linear, branched or cyclic; $NR^1$; or $S(O)_mR^1$, wherein m is 0, 1, 2 or 3 and $R^1$ is as defined above;
  $R^1$, $R^2$ and $R^3$ cannot all be hydrogen;
  $R^4$ is hydrogen; alkyl, alkoxy, alkenyl, alkynyl, haloalkyl, cyanoalkyl or haloalkenyl of from 1 to 10 carbon atoms, linear, branched or cyclic;

or $(CR_2)_nOR^5$, wherein R is hydrogen, or alkyl, alkoxy, alkenyl, alkynyl, haloalkyl, cyanoalkyl or haloalkenyl of from 1 to 10 carbon atoms, linear, branched or cyclic; n is greater than 1; and $R^5$ is hydrogen, cyano, or alkyl, alkenyl, alkoxyalkyl, cyanoalkyl or haloalkyl of from 1 to 10 carbon atoms, linear, branched or cyclic; and
  $X^1$, $X^2$ and $X^3$ are individually hydrogen, methyl, chlorine, fluorine or bromine.

When the cyclohexen-1-yl ring of a compound of this invention is not symmetrical, isomeric compounds can result which differ only in the location of the double bond. Accordingly, it is to be understood that as used in the specification and claims the generic formula I is also meant to encompass the following formula when the cyclohexen-1-yl ring is not symmetrical:

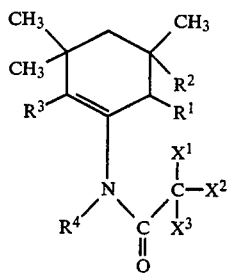

Preferred compounds of this invention include those wherein $R^1$, $R^2$ and $R^3$ are individually hydrogen or alkyl of from 1 to 6 carbon atoms with the proviso that $R^1$, $R^2$ and $R^3$ cannot all be hydrogen. Particularily preferred compounds include those wherein $R^1$, $R^2$ and $R^3$ are individually hydrogen or methyl and $X^1$, $X^2$ and $X^3$ are individually hydrogen or chlorine, with the same proviso as above. Most preferred compounds include those wherein $R^1$, $R^2$, and $R^3$ are individually hydrogen and methyl; $X^1$, $X^2$ and $X^3$ are individually hydrogen or chlorine; and $R^4$ is alkyl, alkoxy, alkenyl, alkynyl, haloalkyl, cyanoalkyl or haloalkenyl of from 1 to 6 carbon atoms, linear, branched or cyclic;

$CR_2CR$;

or $(CR_2)_nOR^5$, wherein R is hydrogen, or alkyl, alkoxy, alkenyl, alkynyl, haloalkyl, cyanoalkyl or haloalkenyl of from 1 to 6 carbon atoms, linear, branched or cyclic; n is greater than 1; and $R^5$ is hydrogen; cyano; or alkyl, alkenyl, alkoxyalkyl, cyanoalkyl or haloalkyl of from 1 to 6 carbon atoms, linear, branched or cyclic, with the same proviso relating to $R^1$, $R^2$, and $R^3$ as above.

Illustrative of the compounds of this invention are the following:

N-3,3,5,5-tetramethylcyclohexen-1-yl chloroacetamide
N-methyl-N-3,3,5,5-tetramethylcyclohexen-1-yl chloroacetamide
N-ethyl-N-3,3,5,5-tetramethylcyclohexen-1-yl chloroacetamide
N-isopropyl-N-3,3,5,5-tetramethylcyclohexen-1-yl chloroacetamide
N-t-butyl-N-3,3,5,5-tetramethylcyclohexen-1-yl chloroacetamide
N-cyclopropyl-N-3,3,5,5-tetramethylcyclohexen-1-yl chloroacetamide
N-cyclopropylmethyl-N-3,3,5,5-tetramethylcyclohexen-1-yl chloroacetamide
N-2-methoxyethyl-N-3,3,5,5-tetramethylcyclohexen-1-yl chloroacetamide
N-3-methoxypropyl-N-3,3,5,5-tetramethylcyclohexen-1-yl chloroacetamide
N-2-ethoxyethyl-N-3,3,5,5-tetramethylcyclohexen-1-yl chloroacetamide
N-(1-methoxymethyl)ethyl-N-3,3,5,5-tetramethylcyclohexen-1-yl chloroacetamide
N-2-iospropoxyethyl-N-3,3,5,5-tetramethylcyclohexen-1-yl chloroacetamide
N-methoxy-N-3,3,5,5-tetramethylcyclohexen-1-yl chloroacetamide
N-ethoxy-N-3,3,5,5-tetramethylcyclohexen-1-yl chloroacetamide
N-isopropoxy-N-3,3,5,5-tetramethylcyclohexen-1-yl chloroacetamide
N-2-dimethoxyethyl-N-3,3,5,5-tetramethylcyclohexen-1-yl chloroacetamide
N-allyl-N-3,3,5,5-tetramethylcyclohexen-1-yl chloroacetamide
N-methallyl-N-3,3,5,5-tetramethylcyclohexen-1-yl chloroacetamide
N-propargyl-N-3,3,5,5-tetramethylcyclohexen-1-yl chloroacetamide
N-butyn-2-yl-N-3,3,5,5-tetramethylcyclohexen-1-yl chloroacetamide
N-propyn-1-yl-N-3,3,5,5-tetramethylcyclohexen-1-yl chloroacetamide
N-2-chloroethyl-N-3,3,5,5-tetramethylcyclohexen-1-yl chloroacetamide
N-chloromethyl-N-3,3,5,5-tetrametylcyclohexen-1-yl chloroacetamide
N-trifluoromethyl-N-3,3,5,5-tetramethylcyclohexen-1-yl chloroacetamide
N-2,2,2-trifluoroethyl-N-3,3,5,5-tetramethylcyclohexen-1-yl chloroacetamide
N-cyanomethyl-N-3,3,5,5-tetramethylcyclohexen-1-yl chloroacetamide
N-methoxycarbonylmethyl-N-3,3,5,5-tetramethylcyclohexen-1-yl chloroacetamide
N-(1-methoxycarbonyl)ethyl-N-3,3,5,5-tetramethylcyclohexen-1-yl chloroacetamide
N-(1-methoxymethyl)ethyl-N-3,3,5,5-tetramethylcyclohexen-1-yl chloroacetamide
N-methyl-N-2,3,3,5,5-pentamethylcyclohexen-1-yl chloroacetamide
N-ethyl-N-2,3,3,5,5-pentamethylcyclohexen-1-yl chloroacetamide
N-isopropyl-N-2,3,3,5,5-pentamethylcyclohexen-1-yl chloroacetamide
N-t-butyl-N-2,3,3,5,5-pentamethylcyclohexen-1-yl chloroacetamide
N-cyclopropyl-N-2,3,3,5,5-pentamethylcyclohexen-1-yl chloroacetamide
N-cyclopropylmethyl-N-2,3,3,5,5-pentamethylcyclohexen-1-yl chloroacetamide
N-2-methoxyethyl-N-2,3,3,5,5-pentamethylcyclohexen-1-yl chloroacetamide
N-2-ethoxyethyl-N-2,3,3,5,5-pentamethylcyclohexen-1-yl chloroacetamide
N-(1-methoxymethyl)ethyl-N-2,3,3,5,5-pentamethylcyclohexen-1-yl chloroacetamide
N-methoxy-N-2,3,3,5,5-pentamethylcyclohexen-1-yl chloroacetamide
N-allyl-N-2,3,3,5,5-pentamethylcyclohexen-1-yl chloroacetamide
N-methallyl-N-2,3,3,5,5-pentamethylcyclohexen-1-yl chloroacetamide
N-propargyl-N-2,3,3,5,5-pentamethylcyclohexen-1-yl chloroacetamide
N-2-chloroethyl-N-2,3,3,5,5-pentamethylcyclohexen-1-yl chloroacetamide
N-2,2,2-trifluoroethyl-N-2,3,3,5,5-pentametylcyclohexen-1-yl chloroacetamide
N-cyanomethyl-N-2,3,3,5,5-pentamethylcyclohexen-1-yl chloroacetamide
N-methoxycarbonylmethyl-N-2,3,3,5,5-pentamethylcyclohexen-1-yl chloroacetamide
N-(1-methoxycarbonyl)ethyl-N-2,3,3,5,5-pentamethylcyclohexen-1-yl chloroacetamide
N-methyl-N-2,3,3,5-tetramethylcyclohexen-1-yl chloroacetamide
N-ethyl-N-2,3,3,5-tetramethylcyclohexen-1-yl chloroacetamide
N-isopropyl-N-2,3,3,5-tetramethylcyclohexen-1-yl chloroacetamide
N-t-butyl-N-2,3,3,5-tetramethylcyclohexen-1-yl chloroacetamide
N-cyclopropyl-N-2,3,3,5-tetramethylcyclohexen-1-yl chloroacetamide
N-cyclopropylmethyl-N-2,3,3,5-tetramethylcyclohexen-1-yl chloroacetamide
N-2-methoxyethyl-N-2,3,3,5-tetramethylcyclohexen-1-yl chloroacetamide
N-2-ethoxyethyl-N-2,3,3,5-tetramethylcyclohexen-1-yl chloroacetamide
N-(1-methoxymethyl)ethyl-N-2,3,3,5-tetramethylcyclohexen-1-yl chloroacetamide
N-methoxy-N-2,3,3,5-tetramethylcyclohexen-1-yl chloroacetamide
N-allyl-N-2,3,3,5-tetramethylcyclohexen-1-yl chloroacetamide N-methallyl-N-2,3,3,5-tetramethylcyclohexen-1-yl chloroacetamide
N-propargyl-N-2,3,3,5-tetramethylcyclohexen-1-yl chloroacetamide
N-2-chloroethyl-N-2,3,3,5-tetramethylcyclohexen-1-yl chloroacetamide
N-2,2,2-trifluoroethyl-N-2,3,3,5-tetramethylcyclohexen-1-yl chloroacetamide
N-cyanomethyl-N-2,3,3,5-tetramethylcyclohexen-1-yl chloroacetamide
N-methoxycarbonylmethyl-N-2,3,3,5-tetramethyl cyclohexen-1-yl chloroacetamide
N-(1-methoxycarbonyl)ethyl-N-2,3,3,5-tetramethyl cyclohexen-1-yl chloroacetamide
N-methyl-N-3-ethyl-3,5,5-trimethylcyclohexen-1-yl chloroacetamide
N-isopropyl-N-3-ethyl-3,5,5-trimethylcyclohexen-1-yl chloroacetamide
N-cyclopropyl-N-3-ethyl-3,5,5-trimethylcyclohexen-1-yl chloroacetamide
N-2-methoxyethyl-N-3-ethyl-3,5,5-trimethylcyclohexen-1-yl chloroacetamide
N-allyl-N-3-ethyl-3,5,5-trimethylcyclohexen-1-yl chloroacetamide
N-propargyl-N-3-ethyl-3,5,5-trimethylcyclohexen-1-yl chloroacetamide
N-cyanomethyl-N-3-ethyl-3,5,5-trimethylcyclohexen-1-yl chloroacetamide
N-(1-methoxycarbonyl)ethyl-N-3-ethyl-3,5,5-trimethylcyclohexen-1-yl chloroacetamide
N-methyl-N-3-dimethylamino-3,5,5-trimethylcyclohexen-1-yl chloroacetamide
N-isopropyl-N-3-dimethylamino-3,5,5-trimethylcyclohexen-1-yl chloroacetamide
N-cyclopropylmethyl-N-3-dimethylamino-3,5,5-trimethylcyclohexen-1-yl chloroacetamide
N-2-methoxyethyl-N-3-dimethylamino-3,5,5-trimethylcyclohexen-1-yl chloroacetamide
N-allyl-N-3-dimethylamino-3,5,5-trimethylcyclohexen-1-yl chloroacetamide
N-propargyl-N-3-dimethylamino-3,5,5-trimethylcyclohexen-1-yl chloroacetamide
N-cyanomethyl-N-3-dimethylamino-3,5,5-trimethylcyclohexen-1-yl chloroacetamide
N-(1-methoxycarbonyl)ethyl-N-3-dimethylamino-3,5,5-trimethylcyclohexen-1-yl chloroacetamide
N-methyl-N-3-methylthio-3,5,5-trimethylcyclohexen-1-yl chloroacetamide
N-isopropyl-N-3-methylthio-3,5,5-trimethylcyclohexen-1-yl chloroacetamide
N-cyclopropylmethyl-N-3-methylthio-3,5,5-trimethylcyclohexen-1-yl chloroacetamide
N-2-methoxyethyl-N-3-methylthio-3,5,5-trimethylcyclohexen-1-yl chloroacetamide
N-allyl-N-3-methylthio-3,5,5-trimethylcyclohexen-1-yl chloroacetamide
N-propargyl-N-3-methylthio-3,5,5-trimethylcyclohexen-1-yl chloroacetamide
N-cyanomethyl-N-3-methylthio-3,5,5-trimethylcyclohexen-1-yl chloroacetamide
N-(1-methoxycarbonyl)ethyl-N-3-methylthio-3,5,5-trimethylcyclohexen-1-yl chloroacetamide
N-methyl-N-2-cyano-3,5,5-trimethylcyclohexen-1-yl chloroacetamide
N-isopropyl-N-2-cyano-3,5,5-trimethylcyclohexen-1-yl chloroacetamide
N-cyclopropylmethyl-N-2-cyano-3,5,5-trimethylcyclohexen-1-yl chloroacetamide
N-2-methoxyethyl-N-2-cyano-3,5,5-trimethylcyclohexen-1-yl chloroacetamide
N-allyl-N-2-cyano-3,5,5-trimethylcyclohexen-1-yl chloroacetamide
N-propargyl-N-2-cyano-3,5,5-trimethylcyclohexen-1-yl chloroacetamide
N-cyanomethyl-N-2-cyano-3,5,5-trimethylcyclohexen-1-yl chloroacetamide
N-methyl-N-2-cyano-3,5,5,5-tetramethylcyclohexen-1-yl chloroacetamide
N-isopropyl-N-2cyano-3,3,5,5-tetramethylcyclohexen-1-yl chloroacetamide
N-cyclopropylmethyl-N-2-cyano-3,3,5,5-tetramethylcyclohexen-1-yl chloroacetamide
N-2-methoxyethyl-N-2-cyano-3,3,5,5-tetramethyl cyclohexen-1-yl chloroacetamide
N-allyl-N-2-cyano-3,3,5,5-tetramethylcyclohexen-1-yl chloroacetamide
N-propargyl-N-2-cyano-3,3,5,5-tetramethylcyclohexen-1-yl chloroacetamide
N-cyanomethyl-N-2-cyano-3,3,5,5-tetramethylcyclohexen-1-yl chloroacetamide
N-(1-methoxymethyl)ethyl-N-2-cyano-3,3,5,5-tetramethylcyclohexen-1-yl chloroacetamide
N-methyl-N-3,3,5,5-tetramethylcyclohexen-1-yl acetamide
N-isopropyl-N-3,3,5,5-tetramethylcyclohexen-1-yl dichloroacetamide
N-cyclopropylmethyl-N-3,3,5,5-tetramethylcyclohexen-1-yl trichloroacetamide
N-2-methoxyethyl-N-3,3,5,5-tetramethylcyclohexen-1-yl bromoacetamide
N-allyl-N-3,3,5,5-tetramethylcyclohexen-1-yl iodoacetamide
N-propargyl-N-3,3,5,5-tetramethylcyclohexen-1-yl fluoroacetamide
N-cyanomethyl-N-3,3,5,5-tetramethylcyclohexen-1-yl trimethylacetamide
N-(1-methoxycarbonyl)ethyl-N-3,3,5,5-tetramethyl cyclohexen-1-yl α-methyl-α-chloroacetamide
N-methyl-N-2,3,3,5,5-pentamethylcyclohexen-1-yl acetamide
N-isopropyl-N-2,3,3,5,5-pentamethylcyclohexen-1-yl dichloroacetamide
N-cyclopropylmethyl-N-2,3,3,5,5-pentamethylcyclohexen-1-yl trichloroacetamide
N-2-methoxyethyl-N-2,3,3,5,5-pentamethylcyclohexen-1-yl bromoacetamide
N-allyl-N-2,33,5,5-pentamethylcyclohexen-1-yl iodoacetamide
N-propargyl-N-2,3,3,5,5-pentamethylcyclohexen-1-yl fluoroacetamide
N-cyanomethyl-N-2,3,3,5,5-pentamethylcyclohexen-1-yl trimethylacetamide
N-(1-methoxycarbonyl)ethyl-N-2,3,3,5,5-pentamethyl cyclohexen-1-ylα-methyl-α-chloroacetamide.
N-methyl-N-2,3,5,5-tetramethylcyclohexen-1-yl acetamide
N-isopropyl-N-2,3,5,5-tetramethylcyclohexen-1-yl dichloroacetamide
N-cyclopropylmethyl-N-2,3,5,5-tetramethylcyclohexen-1-yl trichloroacetamide
N-2-methoxyethyl-N-2,3,5,5-tetramethylcyclohexen-1-yl bromoacetamide
N-allyl-N-2,3,5,5-tetramethylcyclohexen-1-yl iodoacetamide
N-propargyl-N-2,3,5,5-tetramethylcyclohexen-1-yl fluoroacetamide N-cyanomethyl-N-2,3,5,5-tetramethylcyclohexen-1-yl trimethylacetamide
N-(1-methoxycarbonyl)ethyl-N-2,3,5,5-tetramethylcyclohexen-1-ylα-methyl-α-chloroacetamide
N-methyl-N-2-ethyl-3,5,5-trimethylcyclohexen-1-yl chloroacetamide
N-isopropyl-N-2-ethyl-3,5,5-trimethylcyclohexen-1-yl chloroacetamide
N-cyclopropylmethyl-N-2-ethyl-3,5,5-trimethylcyclohexen-1-yl chloroacetamide
N-2-methoxyethyl-N-2-ethyl-3,5,5-trimethylcyclohexen-1-yl chloroacetamide
N-allyl-N-2-ethyl-3,5,5-trimethylcyclohexen-1-yl chloroacetamide
N-propargyl-N-2-ethyl-3,5,5-trimethylcyclohexen-1-yl chloroacetamide
N-cyanomethyl-N-2-ethyl-3,5,5-trimethylcyclohexen-1-yl chloroacetamide
N-(1-methoxycarbonyl)ethyl-N-2-ethyl-3,5,5-trimethylcyclohexen-1-yl chloroacetamide
N-methyl-N-2-iospropyl-3,5,5-trimethylcyclohexen-1-yl chloroacetamide
N-isopropyl-N-2-iospropyl-3,5,5-trimethylcyclohexen-1-yl chloroacetamide
N-cyclopropylmethyl-N-2-isopropyl-3,5,5-trimethylcyclohexen-1-yl chloroacetamide
N-2-methoxyethyl-N-2-isopropyl-3,5,5-trimethylcyclohexen-1-yl chloroacetamide
N-allyl-N-2-isopropyl-3,5,5-trimethylcyclohexen-1-yl chloroacetamide
N-propargyl-N-2-isopropyl-3,5,5-trimethylcyclohexen-1-yl chloroacetamide
N-cyanomethyl-N-2-isopropyl-3,5,5-trimethylcyclohexen-1-yl chloroacetamide
N-(1-methoxycarbonyl)ethyl-N-2-isopropyl-3,5,5-trimethylcyclohexen-1-yl chloroacetamide
N-methyl-N-2,3,5,5-tetramethylcyclohexen-1-yl chloroacetamide
N-isopropyl-N-2,3,5,5-tetramethylcyclohexen-1-yl chloroacetamide
N-cyclopropylmethyl-N-2,3,5,5-tetramethylcyclohexen-1-yl chloroacetamide
N-2-methoxyethyl-N-2,3,5,5-tetramethylcyclohexen-1-yl chloroacetamide
N-allyl-N-2,3,5,5-tetramethylcyclohexen-1-yl chloroacetamide
N-propargyl-N-2,3,5,5-tetramethylcyclohexen-1-yl chloroacetamide
N-cyanomethyl-N-2,3,5,5-tetramethylcyclohexen-1-yl chloroacetamide
N-(1-methoxycarbonyl)ethyl-N-2,3,5,5-tetramethylcyclohexen-1-yl chloroacetamide The compounds of the present invention can be synthesized by the method illustrated by the following general reaction scheme:

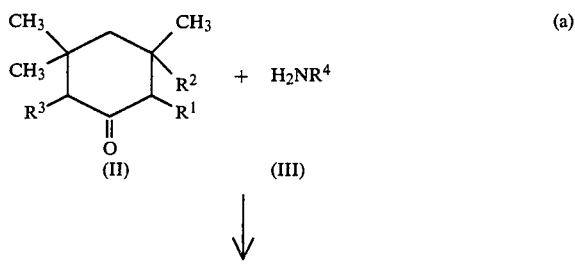

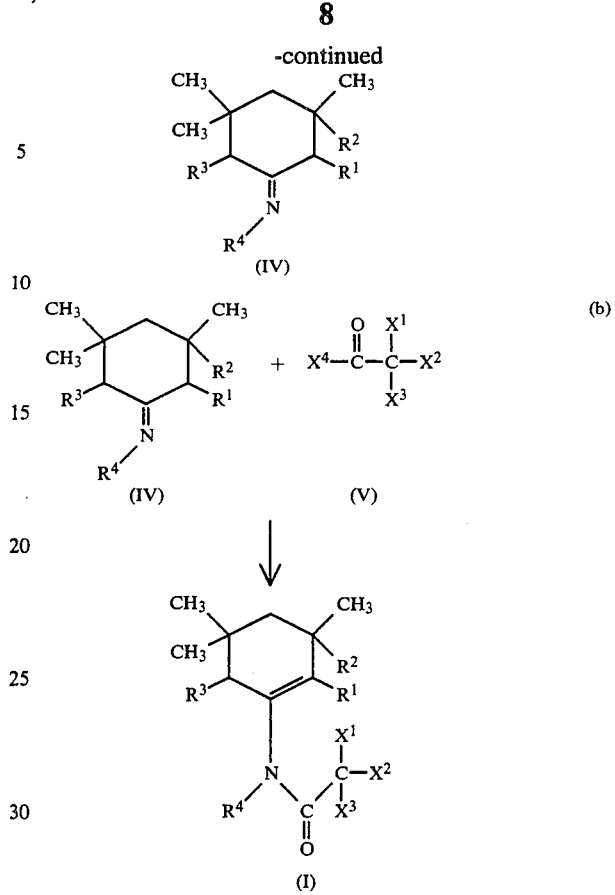

wherein $R^1$, $R^2$, $R^3$, $R^4$, $X^1$, $X^2$ and $X^3$ are as defined above and $X^4$ is bromine, chlorine or fluorine, preferably chlorine.

The method comprises (a) reacting a substituted cyclohexanone (II) with an amine (III) with the elimination of water to form the corresponding imine (IV); and (b) reacting the resulting imine (IV) with an acetyl halide (V) in the presence of an acid-neutralizing reagent to yield the cycloalkenyl acetamide (I).

The substituted cyclohexanones used as starting materials are known in the prior art and are available commercially or may be synthesized according to known methods, such as, e.g., by the method described by Richer, J. C. and MacDougall, W. A., Can. J. Chem. 46: 3703 (1968). Preferable amines are primary amines having linear, branched, or cyclic alkyl or alkoxyalkyl radicals of 1-6 carbon atoms, such as methylamine, ethylamine, propylamine, cyclopropylamine, butylamine, allylamine, methoxyethylamine, ethoxyethylamine, and the like.

The reaction of the cyclohexanones with the amines generally proceeds in the presence of a carrier agent for elimination of the water. The carrier is preferably an inert solvent, such as an aromatic hydrocarbon, dialkyl ether or chlorinated aliphatic hydrocarbon. The starting cyclohexanone in excess may also be used as a carrier. The reaction proceeds at the reflux temperature of the reaction mixture and, therefore, the reaction temperature will vary depending on the carrier agent used.

The elimination of water can be catalytically accelerated by addition of acid or acid reactive catalysts, such as hydrochloric acid, ammonium sulfate or zinc chloride. At times it is advantageous to continuously remove the water produced by the reaction using molecular sieves or by azeotropic distillation.

The resulting imine is then reacted with an acetyl halide, preferably chloroacetyl chloride, in the presence of an acid neutralizing agent at a temperature of from about 0° to about 160° C., preferably from about 0° to about 25° C. Preferable acid neutralizing agents include tertiary amines, pyridine bases and alkali metal carbonates.

When unsymmetrical cyclohexanones are used as starting materials, the resulting double bond in the cycloalkenyl ring can be formed in two different positions. As a result the reaction product can contain a mixture of isomeric compounds of formula (I) which differ only in location of the double bond.

The following examples are provided to illustrate the preparation of the cycloalkenyl acetamides of this invention.

EXAMPLE #1

Synthesis of N-2-methoxyethyl-N-3,3,5,5-tetramethylcyclohexen-1-yl chloroacetamide Part A:

To a 50 ml round bottom flask equipped with a stir bar, reflux condenser and Dean Stark trap was added 3,3,5,5-tetramethylcyclohexanone (5.0 g, 32 mmol), toluene (35 ml), 2-methoxyethylamine (2.4 g, 32 mmol), and a catalytic amount of p-toluenesulfonic acid. The reaction mixture was refluxed for four hours, cooled to room temperature, dried over magnesium sulfate, filtered and concentrated under reduced pressure to yield 6.5 g (96%, 30 mmol) of a yellow liquid. The NMR spectrum of this material confirmed its identity as the desired product:

NMR (CDCl$_3$) δ 3.43–3.67 (m, 4H), 3.36 (s, 3H), 2.15 (s, 4H), 1.42 (s, 2H), 1.04 (s, 12H).

Part B:

To a 100 ml round bottom flask equipped with a stir bar was added the imine (6.5 g, 30.8 mmol) and toluene (30 ml). The resulting solution was cooled via an ice bath before adding chloroacetyl chloride (3.48 g, 30.8 mmol) dropwise. The reaction was stirred for thirty minutes before adding triethylamine (3.6 , 36 mmol) which caused an immediate precipitate to form (triethylamine.HCl). The suspension was stirred an additional hour at room temperature. The precipitate was filtered off, and the filtrate washed with water (2×50 ml), dried over magnesium sulfate, filtered and concentrated down under reduced pressure to afford a dark oil. This crude product was purified via silica gel flash chromatography using a 30% ethyl acetate/70% hexane eluent to yield 4.36 g (49%, 15 mmol) of the desired chloroacetamide.

Analysis for C$_{15}$H$_{26}$Cl$_1$N$_1$O$_2$. Calculated: C, 62.72; H, 9.06; N, 4.88. Found: C, 62.40; H, 9.05; N, 4.65.

EXAMPLE #3

Synthesis of N-allyl-N-3,3,5,5-tetramethylcyclohexen-1-yl chloroacetamide

Part A:

To a 50 ml round-bottom flask equipped with a stir bar, reflux condenser and Dean Starke trap was added 3,3,5,5-tetramethylcyclohexanone (3.0 g, 19 mmol), benzene (35 mls), allylamine (1.2 g, 21 mmol), and a catalytic amount of ammonium sulfate (0.3 g, 2.2 mmol). The reaction mixture was refluxed for seventy-two hours, cooled to room temperature, dried over magnesium sulfate, filtered and concentrated under reduced pressure to afford 3.8 g (100%, 19 mmol) of a yellow oil.

Part B:

To a 50 ml round-bottom flask equipped with a stir bar was added the imine (3.8 g, 19 mmol) and benzene (35 mls). The resulting solution was cooled via an ice bath before adding chloroacetyl chloride (2.2 g, 19 mmol) dropwise. The reaction was stirred for thirty minutes before adding triethylamine (3.6 g, 36 mmol) which caused an immediate precipitate to form (triethylamine.HCl). The suspension was stirred an additional 1½ hours at room temperature. The precipitate was filtered off and the filtrate evaporated under reduced pressure to afford a dark oil. The crude product was purified via silica gel flash chromatography using 40% ethyl acetate/60% hexane eluent to yield 3.4 g (64%, 12.6 mmol) of the desired chloroacetamide as a yellow oil.

Analysis for C$_{15}$H$_{24}$Cl$_1$N$_1$O$_1$. Calculated: C, 66.91; H, 8.92; N, 5.20. Found: C, 66.65; H, 8.92; N, 5.64.

EXAMPLE #9

Synthesis of N-cyloropropyl-N-3,3,5,5-tetramethylcyclohexen-1-yl chloroacetamide Part A:

To a 50 ml round-bottom flask equipped with a stir bar was added 3,3,5,5-tetramethylcyclohexanone (5.0 g, 32 mmol), toluene (30 mls), cyclopropylamine (1.8 g, 32 mmol), and a catalytic amount of ammonium sulfate (0.5 g, 3.8 mmol). The stoppered reaction mixture was stirred at room temperature for four days, dried over magnesium sulfate, filtered and evaporated under reduced pressure to afford 5.0 g (~80%) of the crude imine as a yellow oil.

Part B:

To a 100 ml round-bottom flask equipped with a stir bar was added the imine (2.5 g, 13 mmol) and toluene (40 mls). The resulting solution was cooled via an ice bath before adding chloroacetyl chloride (1.5 g, 13 mmol) dropwise. The reaction was stirred for thirty minutes before adding triethylamine (3.6 g, 36 mmol) which caused an immediate precipitate to form (triethylamine.HCl). The suspension was stirred an additional hour at room temperature. The precipitate was filtered off and the filtrate evaporated under reduced pressure to afford an orange oil. This crude product was purified via silica gel flash chromatography using a 30% ethyl acetate/70% hexane eluent to yield 2.2 g (63%) of an oil which crystallized on standing, mp 49°–52° C.

Analysis for C$_{15}$H$_{24}$Cl$_1$N$_1$O$_1$. Calculated: C, 66.77; H, 8.97; N, 5.19. Found: C, 66.71; H, 8.53; N, 5.04.

EXAMPLE #12

Synthesis of N-2-methoxyethyl-N-2,3,5,5-tetramethylcyclohexen-1-yl chloroacetamide Part A:

To a 50 ml round-bottom flask equipped with a stir bar, reflux condenser, and Dean Starke trap was added 2,3,5,5-tetramethylcyclohexanone (3.0 g, 19 mmol), toluene (25 mls) and 2-methoxyethylamine (2.6 g, 35 mmol). The resulting solution was refluxed for four days, cooled to room temperature, dried over magnesium sulfate, filtered and evaporated under reduced pressure to afford 3.4 g (83%, 16 mmol) of the imine as an orange oil.

and the analyticaal data are set forth in Table I below.

TABLE 1

Physical Properties of Cycloalkenyl Acetamide Herbicides

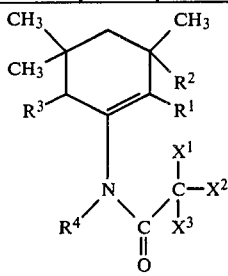

| | Molecular Formula | $R_1$ | $R_2$ | $R_3$ | $R_4$ | $X_1$ | $X_2$ | $X_3$ | M.P. (°C.) | Calculated C | H | N | Found C | H | N |
|---|---|---|---|---|---|---|---|---|---|---|---|---|---|---|---|
| 1 | $C_{15}H_{26}Cl_1N_1O_2$ | H | $CH_3$ | H | $CH_3OCH_2CH_2-$ | H | H | Cl | — | 62.72 | 9.06 | 4.88 | 62.40 | 9.05 | 4.65 |
| 2 | $C_{15}H_{26}Cl_1N_1O_1$ | H | $CH_3$ | H | $(CH_3)_2CH-$ | H | H | Cl | — | 66.42 | 9.59 | 5.17 | 64.36 | 9.19 | 4.25 |
| 3 | $C_{15}H_{24}Cl_1N_1O_1$ | H | $CH_3$ | H | $CH_2=CHCH_2-$ | H | H | Cl | — | 66.91 | 8.92 | 5.20 | 66.65 | 8.92 | 5.64 |
| 4 | $C_{14}H_{21}Cl_1N_2O_1$ | H | $CH_3$ | H | $N\equiv CCH_2$ | H | H | Cl | 38–42 | 62.56 | 7.88 | 10.42 | 63.00 | 7.44 | 10.33 |
| 5 | $C_{16}H_{26}Cl_1N_1O_1$ | H | $CH_3$ | H | $CH_2=\underset{\underset{CH_3}{\vert}}{C}-CH_2-$ | H | H | Cl | — | 67.61 | 9.15 | 4.93 | 67.25 | 9.37 | 5.57 |
| 6 | $C_{16}H_{28}Cl_1N_1O_3$ | H | $CH_3$ | H | $(CH_3O)_2CHCH_2-$ | H | H | Cl | — | 60.38 | 8.81 | 4.40 | 59.72 | 8.38 | 4.45 |
| 7 | $C_{16}H_{28}Cl_1N_1O_2$ | H | $CH_3$ | H | $CH_3OCH_2\underset{\underset{CH_3}{\vert}}{CH}-$ | H | H | Cl | — | 63.66 | 9.35 | 4.64 | 62.19 | 9.30 | 4.50 |
| 8 | $C_{16}H_{28}Cl_1N_1O_2$ | H | $CH_3$ | H | $CH_3O(CH_2)_3-$ | H | H | Cl | — | 63.66 | 9.35 | 4.64 | 63.41 | 9.42 | 4.80 |
| 9 | $C_{15}H_{24}Cl_1N_1O_1$ | H | $CH_3$ | H | ▷— | H | H | Cl | 49–52 | 66.77 | 8.97 | 5.19 | 66.71 | 8.53 | 5.04 |
| 10 | $C_{16}H_{28}Cl_1N_1O_2$ | $CH_3$ | $CH_3$ | H | $CH_3OCH_2CH_2-$ | H | H | Cl | — | 63.66 | 9.35 | 4.64 | 62.90 | 8.90 | 5.50 |
| 11 | $C_{14}H_{23}Cl_2N_1O_1$ | H | $CH_3$ | H | $ClCH_2CH_2-$ | H | H | Cl | 27–29 | 57.53 | 7.93 | 4.79 | 57.07 | 7.90 | 4.79 |
| 12 | $C_{15}H_{26}Cl_1N_1O_2$ | $CH_3$ | H | H | $CH_3OCH_2CH_2-$ | H | H | Cl | — | 62.50 | 9.03 | 4.86 | 62.10 | 9.20 | 5.41 |

Part B:

To a 100 ml round-bottom flask equipped with a stir bar was added the imine (3.4 g, 16 mmol) and toluene (50 mls). The resulting solution was cooled via an ice bath before adding chloroacetyl chloride (2.2 g, 19 mmol) dropwise. The reaction was stirred for one hour before adding triethylamine (3.6 g, 36 mmol) which caused an immediate precipitate to form (triethylamine.HCl). The suspension was stirred an additional hour at room temperature, filtered and the filtrate evaporated under reduced pressure to afford an amber oil. This crude product was purified via silica gel flash column chromatography using a 40% ethyl acetate/60% hexane eluent to yield 1.90 g (41%, 6.6 mmol) of the desired chloroacetamide as a yellow oil.

Analysis for $C_{15}H_{26}Cl_1N_1O_2$. Calculated: C, 62.50; H, 9.03; N, 4.86. Found: C, 62.10; H, 9.20; N, 5.41.

EXAMPLES 1-12

In a manner similar to that employed in the preceding examples, and using the synthesis scheme previously disclosed, other herbicidal acetamides were prepared. The identity of the substituents on the generic formula and the analyticaal data are set forth in Table I below.

The compounds of this invention are effective as herbicides in partial or total inhibition of undesirable vegetation and exhibit excellent selectivity in crops of cultivated plants, dry-land and flooded.

Table II summarizes the results of tests conducted to determine the pre-emergent herbicidal activity and selectivity of these compounds with respect to dry-land plants.

The dry-land test was conducted as follows: Seeds of the type of plants shown in Table II were sown in fresh soil. The soil was sprayed with a solution of the test compounds immediately after the seeds were planted. The solution was about 1% by weight solution of the test compound in acetone.

Approximately three weeks after the spray applications, the herbicidal activity of the compound was determined by visual observation of the treated areas in comparison with untreated controls. These observations are reported in Table II on a scale of 0 to 100% control of plant growth.

The results of this test clearly demonstrate the excellent pre-emergent selectivity and broad-range activity of the compounds of this invention with respect to dry-land crops and weeds.

TABLE II

PREEMERGENT HERBICIDAL ACTIVITY-DRY LAND TEST-PERCENT CONTROL

| COMPOUND OF EXAMPLE | | | |
|---|---|---|---|
| 1 | 2 | 3 | 4 |

TABLE II-continued
PREEMERGENT HERBICIDAL ACTIVITY-DRY LAND TEST-PERCENT CONTROL

|  | APPLICATION RATE LB/ACRE | | | | | | | | | | | | | | | |
|---|---|---|---|---|---|---|---|---|---|---|---|---|---|---|---|---|
|  | 0.5 | 1 | 2 | 4 | 0.5 | 1 | 2 | 4 | 0.5 | 1 | 2 | 4 | 0.5 | 1 | 2 | 4 |
| SOYBEAN | 0 | 0 | 0 | 6 | — | 0 | 0 | 2 | 0 | 0 | 0 | 6 | — | 0 | 0 | 0 |
| COTTON | 0 | 0 | 0 | 6 | — | 0 | 2 | 6 | 0 | 0 | 2 | 20 | — | 0 | 0 | 6 |
| SUGARBEET | 0 | 0 | 0 | 2 | — | 32 | 12 | 12 | 0 | 2 | 2 | 100 | — | 0 | 20 | 20 |
| CORN | 0 | 0 | 0 | 0 | — | 0 | 0 | 0 | 0 | 0 | 0 | 0 | — | 0 | 0 | 0 |
| GIANT FOXTAIL | 88 | 99 | 100 | 100 | — | 100 | 100 | 100 | 88 | 93 | 100 | 100 | — | 72 | 83 | 100 |
| BARNYARD GRASS | 52 | 76 | 98 | 98 | — | 88 | 38 | 98 | 82 | 75 | 85 | 86 | — | 41 | 88 | 100 |
| WILD OATS | 32 | 44 | 63 | 73 | — | 41 | 62 | 99 | 0 | 22 | 44 | 66 | — | 0 | 54 | 62 |
| DOWNY BROME | 53 | 82 | 100 | 100 | — | 100 | 100 | 100 | 53 | 100 | 100 | 100 | — | 88 | 100 | 100 |
| YELLOW NUTSEDGE | 100 | 100 | 100 | 100 | — | 100 | 84 | 100 | 55 | 100 | 100 | 100 | — | 100 | 100 | 100 |

|  | COMPOUND OF EXAMPLE | | | | | | | | | | | | | | | |
|---|---|---|---|---|---|---|---|---|---|---|---|---|---|---|---|---|
|  | 5 | | | | 6 | | | | 7 | | | | 8 | | | |
|  | APPLICATION RATE LB/ACRE | | | | | | | | | | | | | | | |
|  | 0.5 | 1 | 2 | 4 | 0.5 | 1 | 2 | 4 | 0.5 | 1 | 2 | 4 | 0.5 | 1 | 2 | 4 |
| SOYBEAN | — | 0 | 0 | 0 | — | 0 | 0 | 0 | — | 0 | 0 | 6 | — | 0 | 0 | 0 |
| COTTON | — | 0 | 0 | 2 | — | 2 | 6 | 6 | — | 2 | 2 | 6 | — | 2 | 2 | 2 |
| SUGARBEET | — | 100 | 21 | 21 | — | 0 | 10 | 10 | — | 20 | 20 | 20 | — | 2 | 2 | 2 |
| CORN | — | 0 | 0 | 2 | — | 0 | 0 | 0 | — | 0 | 0 | 0 | — | 0 | 0 | 0 |
| GIANT FOXTAIL | — | 100 | 100 | 100 | — | 72 | 73 | 73 | — | 100 | 100 | 100 | — | 2 | 63 | 100 |
| BARNYARD GRASS | — | 30 | 77 | 100 | — | 20 | 20 | 45 | — | 99 | 100 | 100 | — | 10 | 53 | 88 |
| WILD OATS | — | 20 | 50 | 50 | — | 20 | 20 | 33 | — | 30 | 70 | 99 | — | 10 | 21 | 42 |
| DOWNY BROME | — | 0 | 30 | 100 | — | 0 | 0 | 0 | — | 0 | 0 | 20 | — | 0 | 0 | 0 |
| YELLOW NUTSEDGE | — | 0 | 0 | 0 | — | 0 | 0 | 0 | — | 0 | 0 | 0 | — | 0 | 100 | 100 |

|  | COMPOUND OF EXAMPLE | | | | | | | | | | | |
|---|---|---|---|---|---|---|---|---|---|---|---|---|
|  | 9 | | | | 10 | | | | 12 | | | |
|  | APPLICATION RATE LB/ACRE | | | | | | | | | | | |
|  | 0.5 | 1 | 2 | 4 | 0.5 | 1 | 2 | 4 | 0.5 | 1 | 2 | 4 |
| SOYBEAN | — | 0 | 0 | 0 | — | 2 | 30 | 56 | 0 | 0 | 2 | — |
| COTTON | — | 0 | 0 | 2 | — | 2 | 6 | 14 | 0 | 0 | 0 | — |
| SUGARBEET | — | 40 | 30 | 30 | — | 0 | 0 | 6 | 2 | 0 | 0 | — |
| CORN | — | 0 | 0 | 0 | — | 0 | 2 | 6 | 2 | 2 | 0 | — |
| GIANT FOXTAIL | — | 100 | 99 | 100 | — | 99 | 100 | 100 | 90 | 95 | 100 | — |
| BARNYARD GRASS | — | 93 | 97 | 100 | — | 98 | 100 | 100 | 90 | 99 | 99 | — |
| WILD OATS | — | — | — | — | — | — | — | — | 0 | 2 | 2 | — |
| DOWNY BROME | — | 60 | 99 | 100 | — | 100 | 100 | 100 | — | — | — | — |
| YELLOW | — | — | — | — | — | — | — | — | 100 | 100 | 100 | — |

—Compound was not tested.

Table III summarizes the results of tests conducted to determine the activity and selectivity on plants grown under flooded conditions.

The flooded test was conducted as follows: Rice seedlings (var. Starbonnet) were established in nursery flats containing 50% pearlite and 50% vermiculite. When seedlings were in their second to third leaf (approximately 6 inches tall), they were transplanted into test flats containing screened field soil, one row per flat, 15 seedlings per row. Rice plants were allowed to establish in the flats for 3 days before weed seeds were planted. Weed seeds were planted one row each and include: red rice, crabgrass, barnyard grass, sprangle top and rice (preemergent). The flats were sprayed with a solution of test compound such that the row of transplanted rice is treated post-emergent and the weed and rice weed are treated pre-emergent. The treated flats were flooded to a depth of 1.5 cm when the weeds seeded in the control (non-treated) flats emerged. The containers were flushed with tap water every 3 to 4 days to suppress algae growth.

Two weeks after the treatment, the activity/selectivity of the test compound was determined by visual observation of the treated flats in comparison with untreated flats. These observations are reported in Table III on a scale of 0 to 100% control of plant growth.

In order to illustrate the unexpected selectivity properties of repesentative compounds of this invention with respect to flooded rice, direct comparisons were made between compounds of this invention with analogous compounds disclosed in U.S. Pat. Nos. 4,351,667 and 4,319,918 utilizing the flooded test described above.

The prior art compounds tested were:

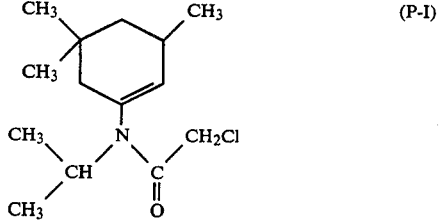

(P-I)

[disclosed in U.S. Pat. No. 4,319,918] and

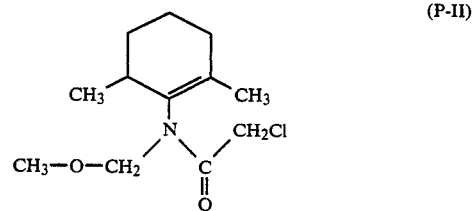

(P-II)

[disclosed in U.S. Pat. No. 4,351,667]

The results of this test demonstrate the superior selectivity of the acetamides of this invention for post-emergent crops of flooded rice while maintaining a high level of effectiveness against a broad range of undesired vegetation. The homologous compounds of the prior art, i.e. P-I and P-II, do not exhibit an acceptable level of selectivity for post-emergent crops of flooded rice.

tions are reported in Table IV on a scale of 0 to 100% control of plant growth.

TABLE IV*

| Compound Of Example | POST-EMERGENT HERBICIDAL ACTIVITY DRY LAND TEST - PERCENT CONTROL | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| SNAPBEANS | 22 | 10 | 43 | 22 | 30 | 10 | 14 | 10 | 33 | 40 | 32 | 14 |
| YELLOW NUTSEDGE | — | — | — | — | — | — | 0 | 10 | — | 30 | 30 | — |
| CRABGRASS | 65 | 26 | 40 | 32 | 26 | 22 | 46 | 74 | 59 | 78 | 76 | 91 |
| BARNYARD GRASS | 44 | 45 | 32 | 10 | 26 | 26 | 59 | 45 | 14 | 65 | 40 | 80 |
| MORNING GLORY | 14 | 10 | 14 | 38 | 10 | 10 | 0 | 54 | 80 | 19 | 35 | 65 |
| DOWNY BROME | 14 | — | — | 0 | — | 0 | 12 | 0 | 10 | 0 | 0 | 0 |
| VELVET LEAF | 14 | — | 19 | 26 | 14 | 0 | 0 | 0 | 30 | 20 | 0 | 12 |
| WILD OATS | — | 12 | 8 | 10 | — | 0 | 0 | 10 | 20 | 0 | 0 | 26 |
| MARIGOLD | 14 | — | 10 | 0 | 10 | 10 | 0 | 30 | 40 | 32 | 10 | — |
| GIANT FOXTAIL | 44 | 20 | 10 | 19 | 30 | 20 | 35 | 26 | 22 | 78 | 50 | 93 |
| FLAX | 72 | 10 | 10 | 10 | 11 | 0 | 10 | 10 | 78 | 26 | 12 | 54 |
| SORGHUM | 14 | 26 | 20 | 0 | 10 | 14 | 10 | 33 | 30 | 22 | 10 | 19 |
| MUSTARD | 14 | 20 | 10 | 10 | 10 | 10 | 19 | 12 | 10 | 10 | 10 | 20 |
| NIGHTSHADE | 52 | 10 | 10 | 33 | 26 | 10 | 0 | 10 | 40 | 50 | 10 | 77 |
| TEAWEED | 21 | — | 26 | 14 | — | 0 | 0 | 10 | 56 | 30 | 6 | 10 |
| QUACK GRASS | 14 | 10 | 10 | 0 | 20 | — | 10 | 26 | 10 | 20 | 40 | 10 |

*Application rate = 8 lbs./acre.
— Compound was not tested

It will be understood that the plant species employed in the above tests are merely representative of a wide variety of plants that can be controlled by the use of the compounds of this invention. The compounds contemplated in this invention may be applied according to

TABLE III

| | HERBICIDAL ACTIVITY-FLOODED LAND TEST-PERCENT CONTROL | | | | | | | | | | | | | | | | | |
|---|---|---|---|---|---|---|---|---|---|---|---|---|---|---|---|---|---|---|
| | COMPOUND OF EXAMPLE | | | | | | | | | | | | | | | | | |
| | 1 | | | 2 | | | 3 | | | 4 | | | 9 | | | 10 | | |
| | APPLICATION RATE LB/ACRE | | | | | | | | | | | | | | | | | |
| | 1 | 2 | 4 | 1 | 2 | 4 | 1 | 2 | 4 | 1 | 2 | 4 | 1 | 2 | 4 | 1 | 2 | 4 |
| RICE (POST) | 0 | 6 | 20 | 5 | 5 | — | 0 | 0 | 0 | 0 | 0 | 0 | 0 | 0 | 0 | 0 | 0 | — |
| SPRANGLE TOP | 100 | 100 | 100 | 100 | 100 | — | 100 | 100 | 100 | 100 | 100 | 100 | 30 | 72 | 100 | 100 | 100 | — |
| RED RICE | 90 | 100 | 100 | 100 | 100 | — | 0 | 90 | 100 | 0 | 0 | 95 | 0 | 0 | 30 | 52 | 55 | — |
| LARGE CRABGRASS | 100 | 100 | 100 | 100 | 100 | — | 90 | 100 | 100 | 30 | 56 | 100 | 2 | 100 | 100 | 97 | 99 | — |
| BARNYARD GRASS | 100 | 100 | 100 | 99 | 100 | — | 95 | 100 | 100 | 0 | 82 | 95 | 2 | 88 | 98 | 75 | 99 | — |
| YELLOW NUTSEDGE | — | — | — | — | — | — | — | — | — | — | — | — | — | — | — | — | — | — |
| RICE (PRE) | 94 | 100 | 100 | 100 | 100 | — | 95 | 100 | 100 | 95 | 100 | — | 0 | 20 | 14 | 0 | 83 | — |

| | COMPOUND OF EXAMPLE | | | | | | | | |
|---|---|---|---|---|---|---|---|---|---|
| | 12 | | | P-I | | | P-II | | |
| | APPLICATION RATE LB/ACRE | | | | | | | | |
| | 1 | 2 | 4 | 1 | 2 | 4 | 1 | 2 | 4 |
| RICE (POST) | 0 | 0 | 2 | 26 | 62 | 58 | 46 | 59 | — |
| SPRANGLE TOP | 100 | 100 | 100 | 100 | 100 | 100 | 100 | 100 | — |
| RED RICE | 80 | 90 | 100 | 100 | 100 | 100 | 100 | 100 | — |
| LARGE CRABGRASS | 100 | 100 | 100 | 100 | 100 | 100 | 100 | 100 | — |
| BARNYARD GRASS | 99 | 100 | 100 | 100 | 100 | 100 | 87 | 100 | — |
| YELLOW NUTSEDGE | — | — | — | 100 | 100 | 100 | — | — | — |
| RICE (PRE) | — | — | — | 100 | 100 | 100 | 100 | 100 | — |

— Compound was not tested.

Additional testing was conducted to determine the post-emergent activity of representative compounds of this invention under dry-land conditions. In this test seeds of the type of plants as shown in Table IV were sown in fresh soil. Approximately two weeks after the seeds are sown, the soil and developing plants were sprayed with the test compound at a rate of 8 lbs/acre from about a 1% by weight solution of the test compound in acetone. Approximately three weeks after spray applications, the activity of the compound was determined by visual observation of the treated areas in comparison with untreated controls. These observamethods known to those skilled in the art. Compositions containing the compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agent.

The choice of dispersing and emulsifying agents and the amount employed in dictated by the nature of the composition and the ability of the agent to facilitate the dispersion of the compound. Generally, it is desirable to use as little of the agent as is possible. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth fullers earth, and the like. In the formulation of the wettable powders the aforementioned dispersing agents as well as lignosulfonates can be included.

The required amount of the compound contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active ingredients per acre.

It will be appreciated that mixtures of the active compounds of this invention may be employed as well as combinations of the active compounds of this invention with other biologically active compounds.

What is claimed is:

1. A compound of the formula

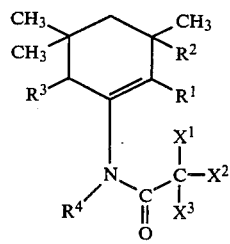

wherein $R^1$ and $R^3$ are individually hydrogen; cyano; or alkyl, alkenyl, alkoxyalkyl, cyanoalkyl or haloalkyl of from 1 to 10 carbon atoms, linear, branched or cyclic;

$R^2$ is hydrogen; alkyl, alkoxyalkyl, alkenyl, alkynyl, haloalkyl, cyanoalkyl or haloalkenyl of from 1 to 10 carbon atoms, linear, branched or cyclic; $NR^1$, or $S(O)_mR^1$ wherein m is 0, 1, 2 or 3 and $R^1$ is as defined above;

$R^1$, $R^2$ and $R^3$ cannot all be hydrogen;

$R^4$ is hydrogen, alkyl, alkoxy, alkenyl, alkynyl, haloalkyl, cyanoalkyl or haloalkenyl of from 1 to 10 carbon atoms, linear, branched or cyclic;

or $2)_nOR^5$, wherein R is hydrogen, or alkyl, alkoxy, alkenyl, alkynyl, haloalkyl, cyanoalkyl or haloalkenyl of from 1 to 10 carbon atoms, linear, branched or cyclic; n is greater than 1; and $R^5$ is hydrogen, cyano, or alkyl, alkenyl, alkoxyalkyl, cyanoalkyl or haloalkyl of from 1 to 10 carbon atoms, linear, branched or cyclic; and $X^1$, $X^2$ and $X^3$ are individually hydrogen, methyl, chlorine, fluorine or bromine.

2. A compound of the formula

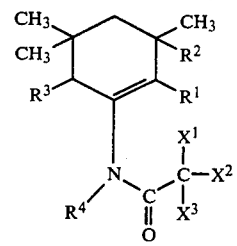

wherein $R^1$ and $R^3$ are individually hydrogen; cyano; or alkyl, alkenyl, alkoxyalkyl, cyanoalkyl or haloalkyl of from 1 to 10 carbon atoms, linear, branched or cyclic;

$R^2$ is hydrogen; alkoxyalkyl, alkenyl, alkynyl, haloalkyl, cyanoalkyl or haloalkenyl of from 1 to 10 carbon atoms, linear, branched or cyclic; $NR^1$, or $S(O)_mR^1$ wherein m is 0, 1, 2 or 3 and $R^1$ is as defined above;

$R^1$, $R^2$ and $R^3$ cannot all be hydrogen;

$R^4$ is hydrogen, alkyl, alkoxy, alkenyl, alkynyl, haloalkyl, cyanoalkyl or haloalkenyl of from 1 to 10 carbon atoms, linear, branched or cyclic;

or $2)_nOR^5$, wherein R is hydrogen, or alkyl, alkoxy, alkenyl, alkynyl, haloalkyl, cyanoalkyl or haloalkenyl of from 1 to 10 carbon atoms, linear, branched or cyclic; n is greater than 1; and $R^5$ is hydrogen, cyano, or alkyl, alkenyl, alkoxyalkyl, cyanoalkyl or haloalkyl of from 1 to 10 carbon atoms, linear, branched or cyclic; and $x^1$, $X^2$ and $X^3$ are individually hydrogen, methyl, chlorine, fluorine or bromine.

3. A compound of the formula

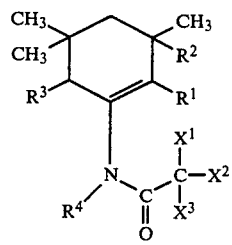

wherein $R^1$, $R^2$ and $R^3$ are individually hydrogen or alkyl of from one to six carbon atoms with the proviso that $R^1$, $R^2$ are not all hydrogen;

$R^4$ is hydrogen, alkyl alkoxyalkyl, alkenyl, alkynyl, haloalkyl, cyanoalkyl or haloalkenyl of from 1 to 6 carbon atoms, linear, branched or cyclic;

or $(CR_2)_nOR^5$, wherein R is hydrogen, or alkyl, alkoxy, alkenyl, alkynyl, haloalkyl, cyanoalkyl or haloalkenyl of from 1 to 6 carbon atoms, linear, branched or cyclic; n is greater than 1; and $R^5$ is hydrogen, cyano or alkyl, alkenyl, alkoxyalkyl, cyanoalkyl or haloalkyl of from 1 to 6 carbon atoms, linear, branched or cyclic; and $X^1$, $X^2$ and $X^3$ are individually hydrogen, methyl, chlorine, fluorine or bromine.

4. A compound as recited in claim 3, wherein $R^1$, $R^2$ and $R^3$ are individually hydrogen or methyl with the proviso that $R^1$, $R^2$ and $R^3$ are not all hydrogen.

5. A compound as recited in claim 3, wherein $X^1$, $X^2$ and $X^3$ are individually hydrogen or chlorine.

6. A compound as recited in claim 3 wherein
$R^1$ and $R^3$ are hydrogen;
$R^2$ is methyl; and

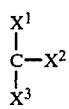

is $CH_2Cl$ or $CHCl_2$.

7. A compound as recited in claim 3 wherein
$R^1$ and $R^2$ are methyl;
$R^3$ is hydrogen; and

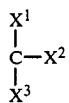

is $CH_2Cl$.

8. A compound as recited in claim 3 wherein
$R^1$ is methyl;
$R^2$ and $R^3$ are hydrogen; and

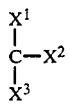

is $CH_2Cl$.

9. A compound as recited in claim 1 which is N-2-methoxyethyl-N-3,3,5,5-tetramethylcyclohexen-1-yl chloroacetamide.

10. A compound as recited in claim 1 which is N-cyanomethyl-N-3,3,5,5-tetramethylcyclohexen-1-yl chloroacetamide.

11. A compound as recited in claim 1 which is N-allyl-N-3,3,5,5-tetramethylcyclohexen-1-yl chloroacetamide.

12. An herbicidal composition comprising an acceptable carrier and an herbicidally effective amount of the compound of claim 1.

13. An herbicidal composition comprising an acceptable carrier and an herbicidally effective amount of the compound of claim 3.

14. An herbicidal composition comprising an acceptable carrier and an herbicidally effective amount of the compound of claim 4.

15. An herbicidal composition comprising an acceptable carrier and an herbicidally effective amount of the compound of claim 9.

16. An herbicidal composition comprising an acceptable carrier and an herbicidally effective amount of the compound of claim 10.

17. An herbicidal composition comprising an acceptable carrier and an herbicidally effective amount of the compound of claim 11.

18. A method for selectively controlling undesirable vegetation in crops of cultivated plants which comprises applying to the locus of the crops an herbicidally effective amount of the compound of claim 1.

19. A method for selectively controlling undesirable vegetation in crops of cultivated plants which comprises applying to the locus of the crops an herbicidally effective amount of the compound of claim 3.

20. A method for selectively controlling undesirable vegetation in crops of cultivated plants which comprises applying to the locus of the crops an herbicidally effective amount of the compound of claim 4.

21. A method for selectivity controlling undesirable vegetation in crops of cultivated plants which comprises applying to the locus of the crops an herbicidally effective amount of the compound of claim 9.

22. A method for seletively controlling undesirable vegetation in crops of cultivated plants which comprises applying to the locus of the crops an herbicidally effective amoun of the compound of claim 10.

23. A. method for selectively controlling undesirable vegetation in crops of cultivated plants which comprises applying to the locus of the crops an herbicidally effective amount of the compound of claim 11.

24. A method as recited in claim 18 wherein said crops of cultivated plants are crops of flooded rice.

25. A method as recited in claim 19 wherein said crops of cultivated plants are crops of flooded rice.

26. A method as recited in claim 18 wherein said crops of cultivated plants are crops of transplanted rice.

27. A method as recited in claim 19 wherein said crops of cultivated plants are crops of transplanted rice.

* * * * *

UNITED STATES PATENT AND TRADEMARK OFFICE
CERTIFICATE OF CORRECTION

PATENT NO. : 4,608,082
DATED : August 26, 1986
INVENTOR(S) : Todd A. Craig and John J. Jachetta It is certified that error appears in the above-identified patent and that said Letters Patent is hereby corrected as shown below:

Column 2, line 64, change "Particularily" to --Particularly--.

Column 6, line 9, change the "cyano-3,5,5,5" portion of the compound name to --cyano-3,3,5,5--;

Column 6, line 11, change the "N-2cyano" portion of the compound name to --N-2-cyano--;

Column 6, line 15, delete all spaces between the "tetramethyl" portion of the compound name and "cy-";

Column 6, line 39, delete the space between the "tetramethyl" portion of the compound name and "cy-";

Column 6, line 49, change the "N-2,33,5,5" portion of the compound name to --N-2,3,3,5,5--;

Column 7, line 24, change the "N-2-iospropyl" portion of the compound name to --N-2-isopropyl--;

Column 9, line 44, change "3.6, 36 mmol" to --3.6 g, 36 mmol--;

Column 9, line 46, change "thylamine.HCl" to --thylamine·HCl--;

Column 10, line 12, change "thylamine.HCl" to --thylamine·HCl--;

Column 10, line 26, change the "N-cyloropropyl" portion of the compound name to --N-cyclopropyl--;

Column 10, line 46, change "thylamine.HCl" to --thylamine·HCl--;

Column 11, line 48, change "thylamine.HCl" to --thylamine·HCl--;

UNITED STATES PATENT AND TRADEMARK OFFICE
CERTIFICATE OF CORRECTION

PATENT NO. : 4,608,082

DATED : August 26, 1986

INVENTOR(S) : Todd A. Craig and John J. Jachetta

It is certified that error appears in the above-identified patent and that said Letters Patent is hereby corrected as shown below:

Column 12, line 1, change "analyticaal" to --analytical--;

Column 13, last line in TABLE II, after "YELLOW", insert --NUTSEDGE--;

Column 17, line 2, change "in" to --is--;

Column 17, line 14, insert a comma between "earth" and "fullers";

Column 17, line 64, change "or 2)$_n$OR$^5$" to --or (CR$_2$)$_n$OR$^5$--;

Column 18, line 39, change "or 2)$_n$OR$^5$" to --or (CR$_2$)$_n$OR$^5$--;

Column 18, line 65, after "R$^2$", insert --and R$^3$--;

Column 18, line 66, insert a comma between "alkyl" and "alkoxyalkyl";

Column 20, line 37, change "selectivity" to --selectively--;

Column 20, line 41, change "seletively" to --selectively--;

Column 20, line 44, change "amoun" to --amount--.

Signed and Sealed this

Third Day of February, 1987

Attest:

DONALD J. QUIGG

Attesting Officer

Commissioner of Patents and Trademarks